US009468709B2

(12) United States Patent
Shippert

(10) Patent No.: US 9,468,709 B2
(45) Date of Patent: Oct. 18, 2016

(54) SYRINGE FILL METHOD AND APPARATUS

(71) Applicant: Ronald D. Shippert, Littleton, CO (US)

(72) Inventor: Ronald D. Shippert, Littleton, CO (US)

(73) Assignee: Shippert Enterprises, LLC, Centennial, CO (US)

( * ) Notice: Subject to any disclaimer, the term of this patent is extended or adjusted under 35 U.S.C. 154(b) by 243 days.

(21) Appl. No.: 14/078,333

(22) Filed: Nov. 12, 2013

(65) Prior Publication Data

US 2014/0130936 A1     May 15, 2014

Related U.S. Application Data

(60) Provisional application No. 61/725,262, filed on Nov. 12, 2012.

(51) Int. Cl.
    *B65B 3/00*        (2006.01)
    *A61M 1/00*       (2006.01)

(52) U.S. Cl.
    CPC ............ *A61M 1/0009* (2013.01); *A61M 1/007* (2014.02); *A61M 1/0058* (2013.01); *A61M 2202/08* (2013.01)

(58) Field of Classification Search
    CPC ....... A61M 1/00; A61M 31/00; B65B 3/003; B65D 31/04; B65D 81/20
    USPC ......... 141/2, 8, 18, 25, 26, 27, 65, 234–237, 141/242, 244; 600/562–571
    See application file for complete search history.

(56) References Cited

U.S. PATENT DOCUMENTS

| 1,138,764 | A | 5/1915 | Kline |
| 3,223,490 | A | 12/1965 | Sacken et al. |
| 3,434,869 | A | 3/1969 | Davidson |
| 3,664,387 | A | 5/1972 | Cates, Jr. |
| 3,693,673 | A | 9/1972 | Oates |
| 3,993,080 | A | 11/1976 | Loseff |
| 4,346,711 | A | 8/1982 | Agdanowski et al. |
| 4,359,049 | A | 11/1982 | Redl et al. |
| 4,447,230 | A | 5/1984 | Gula et al. |

(Continued)

FOREIGN PATENT DOCUMENTS

| EP | 1531881 | 5/2005 |
| EP | 1531882 | 5/2005 |

(Continued)

OTHER PUBLICATIONS

Lee W. Young, International Search Report for International (PCT) Patent Application No. PCT/US 08/59469, mailed Aug. 28, 2008, pp. 1-3.

(Continued)

*Primary Examiner* — Mark A Laurenzi
*Assistant Examiner* — Andrew Schmid
(74) *Attorney, Agent, or Firm* — Sheridan Ross P.C.

(57) ABSTRACT

Tissue collection systems and methods are provided. More particular, a modular system including one or more manifold elements is provided. Each manifold element includes a manifold barrel and a coupler to which a syringe body can be connected. An inlet of a first manifold element is connected to a first manifold cap having an inlet orifice. A second manifold cap having an outlet orifice is connected to the outlet of the first manifold element or to the outlet of a second manifold element. The manifold barrel can include a barrel inlet that is offset from a barrel outlet.

19 Claims, 12 Drawing Sheets

(56) References Cited

U.S. PATENT DOCUMENTS

| | | | |
|---|---|---|---|
| 4,492,258 A | 1/1985 | Lichtenstein et al. | |
| 4,548,207 A | 10/1985 | Reimels | |
| 4,683,884 A | 8/1987 | Hatfield et al. | |
| 4,753,634 A | 6/1988 | Johnson | |
| 4,770,187 A | 9/1988 | Lash et al. | |
| D298,650 S | 11/1988 | Lash | |
| 4,834,703 A | 5/1989 | Dubrul et al. | |
| 4,883,755 A | 11/1989 | Carabasi et al. | |
| 4,957,492 A * | 9/1990 | McVay | A61M 1/0056 600/573 |
| 5,035,708 A | 7/1991 | Alchas et al. | |
| 5,049,146 A | 9/1991 | Bringham et al. | |
| 5,052,999 A * | 10/1991 | Klein | A61M 1/0064 600/571 |
| 5,158,533 A | 10/1992 | Strauss et al. | |
| 5,312,380 A | 5/1994 | Alchas et al. | |
| 5,338,294 A | 8/1994 | Blake, III | |
| 5,352,194 A | 10/1994 | Greco et al. | |
| 5,352,410 A | 10/1994 | Hansen et al. | |
| 5,372,945 A | 12/1994 | Alchas et al. | |
| 5,409,012 A * | 4/1995 | Sahatjian | A61B 10/0275 600/562 |
| 5,441,539 A | 8/1995 | Alchas et al. | |
| 5,569,178 A | 10/1996 | Henley | |
| 5,603,845 A | 2/1997 | Holm | |
| 5,766,134 A | 6/1998 | Lisak et al. | |
| 5,786,207 A | 7/1998 | Katz et al. | |
| 5,804,366 A | 9/1998 | Hu et al. | |
| 5,827,217 A | 10/1998 | Silver et al. | |
| 5,911,700 A | 6/1999 | Mozsary et al. | |
| 5,976,470 A | 11/1999 | Maiefski et al. | |
| 6,013,048 A | 1/2000 | Podany et al. | |
| 6,024,725 A | 2/2000 | Bollinger et al. | |
| 6,258,054 B1 | 7/2001 | Mozsary et al. | |
| 6,299,763 B1 | 10/2001 | Ashman | |
| 6,303,286 B1 | 10/2001 | Dennis et al. | |
| 6,315,756 B1 | 11/2001 | Tankovich | |
| 6,316,247 B1 | 11/2001 | Katz et al. | |
| 6,468,225 B1 | 10/2002 | Lundgren | |
| 6,494,876 B1 | 12/2002 | Fowler et al. | |
| 6,623,733 B1 | 9/2003 | Hossainy et al. | |
| 6,626,890 B2 | 9/2003 | Nguyen et al. | |
| 6,777,234 B1 | 8/2004 | Dennis et al. | |
| 6,905,660 B2 | 6/2005 | Harper et al. | |
| 6,991,765 B2 | 1/2006 | Neilson et al. | |
| 7,097,690 B2 | 8/2006 | Usher et al. | |
| 7,121,309 B2 | 10/2006 | Goemans et al. | |
| 7,204,829 B2 * | 4/2007 | Hung | A61B 10/0045 604/284 |
| 7,335,513 B2 | 2/2008 | Smith et al. | |
| 7,390,484 B2 | 6/2008 | Fraser et al. | |
| 7,687,059 B2 | 3/2010 | Fraser et al. | |
| 7,780,649 B2 | 8/2010 | Shippert | |
| 7,789,872 B2 | 9/2010 | Shippert | |
| 7,794,449 B2 | 9/2010 | Shippert | |
| 8,062,286 B2 | 11/2011 | Shippert | |
| 8,172,832 B1 * | 5/2012 | Gonzalez | A61M 1/0001 604/317 |
| 8,361,042 B1 * | 1/2013 | Gonzalez | A61M 1/0001 604/317 |
| 8,622,997 B2 | 1/2014 | Shippert | |
| 8,632,498 B2 * | 1/2014 | Rimsa | A61M 5/2053 604/121 |
| 8,858,518 B2 * | 10/2014 | Schafer | A61M 1/0005 604/317 |
| 8,887,770 B1 * | 11/2014 | Shippert | B65B 31/04 141/234 |
| 9,039,678 B2 * | 5/2015 | Saxena | A61M 1/0009 604/543 |
| 2002/0146817 A1 | 10/2002 | Cannon et al. | |
| 2002/0198474 A1 | 12/2002 | Becker | |
| 2003/0161816 A1 | 8/2003 | Fraser et al. | |
| 2003/0162707 A1 | 8/2003 | Fraser et al. | |
| 2004/0067219 A1 | 4/2004 | Vida | |
| 2004/0097867 A1 | 5/2004 | Fraser et al. | |
| 2004/0153001 A1 * | 8/2004 | Hung | A61B 10/0041 600/562 |
| 2005/0025755 A1 | 2/2005 | Hedrick | |
| 2005/0084961 A1 | 4/2005 | Hedrick et al. | |
| 2005/0186671 A1 | 8/2005 | Cannon et al. | |
| 2006/0093527 A1 | 5/2006 | Buss | |
| 2006/0213374 A1 * | 9/2006 | Shippert | A61M 1/0062 99/472 |
| 2006/0258004 A1 | 11/2006 | Kosnik et al. | |
| 2007/0100277 A1 * | 5/2007 | Shippert | A61M 1/0062 604/27 |
| 2007/0225686 A1 * | 9/2007 | Shippert | A61M 1/0001 604/542 |
| 2008/0014181 A1 * | 1/2008 | Ariff | A61K 35/12 424/93.7 |
| 2008/0058763 A1 | 3/2008 | Boland et al. | |
| 2008/0154240 A1 * | 6/2008 | Shippert | A61M 1/0001 604/542 |
| 2009/0171242 A1 * | 7/2009 | Hibner | A61B 10/0275 600/566 |
| 2009/0192454 A1 | 7/2009 | Boland et al. | |
| 2009/0287190 A1 * | 11/2009 | Shippert | A61M 1/0001 604/542 |
| 2010/0280496 A1 | 11/2010 | Shippert | |
| 2013/0030322 A1 * | 1/2013 | Levine | A61B 10/0283 600/566 |
| 2014/0130936 A1 * | 5/2014 | Shippert | A61M 1/0009 141/2 |

FOREIGN PATENT DOCUMENTS

| | | |
|---|---|---|
| EP | 1921133 | 5/2008 |
| WO | WO 00/77164 | 12/2000 |
| WO | WO 2004/067065 | 8/2004 |
| WO | WO 2005/011569 | 2/2005 |
| WO | WO 2005/012480 | 2/2005 |
| WO | WO 2005/034843 | 4/2005 |
| WO | WO 2005/095581 | 10/2005 |
| WO | WO 2006/014156 | 2/2006 |
| WO | WO 2006/014159 | 2/2006 |
| WO | WO 2006/022612 | 3/2006 |
| WO | WO 2006/026969 | 3/2006 |
| WO | WO 2006/127007 | 11/2006 |
| WO | WO 2008/137234 | 11/2008 |
| WO | WO 2009/149691 | 12/2009 |

OTHER PUBLICATIONS

Lee W. Young, Written Opinion for International (PCT) Patent Application No. PCT/US 08/59469, mailed Aug. 28, 2008, pp. 1-5.
Genesis Biosystems, Advancing the Science of Skincare, LipiVage, 1 page, at http://www.dermagenesis.com/prodlipivage.cfm, printed Oct. 25, 2004.
Genesis Biosystems, Advancing the Science of Skincare, LipiVage, 3 pages, at http://www.dermagenesis.com/prodlipivage.cfm, printed Mar. 16, 2005.
LipiVage Fat Harvest, Wash & Transfer System, available at www.lipivage.com, Genesis Biosystems, Inc., 2 pages, printed Sep. 21, 2005.
LipiVage, product insert, 2 pages, Aug. 2004.
"Innovative Time-Saving Products, vol. VII," Shippert Medical Technologies Incorporated, Apr. 2010, 40 pages.
Restriction Requirement for U.S. Appl. No. 11/088,598, filed Mar. 23, 2005, mailed Feb. 12, 2009, pp. 1-5.
Office Action for U.S. Appl. No. 11/088,598, mailed Jul. 21, 2009, pp. 1-15.
Final Office Action for U.S. Appl. No. 11/088,598, mailed Mar. 3, 2010, pp. 1-17.
Interview Summary for U.S. Appl. No. 11/088,598, mailed May 19, 2010, 3 pages.
Notice of Allowance and Fee(s) Due for U.S. Appl. No. 11/088,598, mailed Jun. 10, 2010, 8 pages.
Restriction Requirement for U.S. Appl. No. 11/553,920, filed Oct. 27, 2006, mailed Feb. 12, 2009, pp. 1-5.
Office Action for U.S. Appl. No. 11/553,921, mailed Jul. 7, 2009, pp. 1-11.

(56) References Cited

OTHER PUBLICATIONS

Final Office Action for U.S. Appl. No. 11/553,920, mailed Mar. 26, 2010, pp. 1-11.
Interview Summary for U.S. Appl. No. 11/553,920, mailed May 19, 2010, 4 pages.
Notice of Allowance and Fee(s) Due for U.S. Appl. No. 11/553,920, mailed Jun. 10, 2010, 8 pages.
Restriction Requirement for U.S. Appl. No. 11/742,452, filed Apr. 30, 2007, mailed Feb. 20, 2009, pp. 1-5.
Office Action for U.S. Appl. No. 11/742,452, filed Apr. 30, 2007, mailed May 12, 2009, pp. 1-7.
Final Office Action for U.S. Appl. No. 11/742,452, mailed Nov. 6, 2009, pp. 1-10.
Interview Summary for U.S. Appl. No. 11/742,452, mailed Dec. 16, 2009, pp. 1-3.
Notice of Allowance for U.S. Appl. No. 11/742,452, mailed Jan. 4, 2010, pp. 1-4.
Restriction Requirement for U.S. Appl. No. 12/046,300, mailed Aug. 30, 2010, 6 pages.
Official Action for U.S. Appl. No. 12/046,300, mailed Oct. 13, 2010, 33 pages.
Final Official Action for U.S. Appl. No. 12/046,300, mailed Mar. 22, 2011, 7 pages.
Notice of Allowance for U.S. Appl. No. 12/046,300, mailed Sep. 20, 2011, 6 pages.
Official Action for U.S. Appl. No. 13/174,169, mailed Jun. 5, 2014, 7 pages.
Restriction Requirement for U.S. Appl. No. 12/484,781, mailed Jul. 7, 2011, 6 pages.
Official Action for U.S. Appl. No. 12/484,781, mailed Oct. 5, 2011, 10 pages.
Final Official Action for U.S. Appl. No. 12/484,781, mailed Apr. 23, 2012, 12 pages.
Notice of Allowance for U.S. Appl. No. 12/484,781, mailed Sep. 18, 2013, 8 pages.
Official Action for U.S. Appl. No. 13/050,749 mailed Nov. 19, 2013, 6 pages.
Official Action for U.S. Appl. No. 13/050,749 mailed Feb. 12, 2014, 9 pages.
Official Action for U.S. Appl. No. 13/050,749 mailed Jul. 9, 2014, 8 pages.
Official Action for U.S. Appl. No. 13/174,169, mailed Sep. 10, 2014, 8 pages.
Notice of Allowance for U.S. Appl. No. 13/050,749, mailed Sep. 16, 2014, 7 pages.
Official Action for U.S. Appl. No. 13/174,169, mailed May 5, 2015, 11 pages.
Official Action for U.S. Appl. No. 13/174,169, mailed Nov. 19, 2015, 10 pages.

* cited by examiner

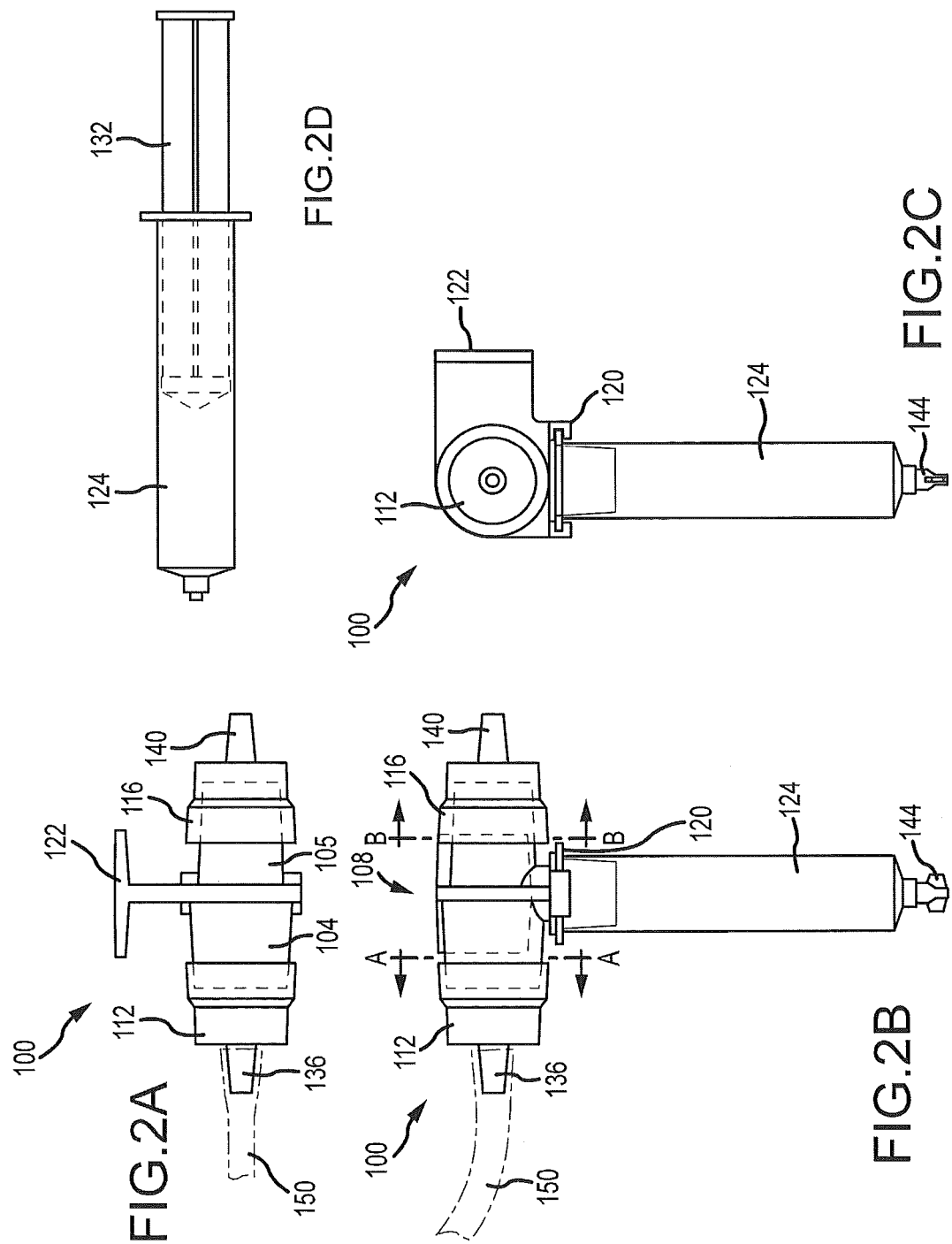

SECTION A-A

SECTION B-B

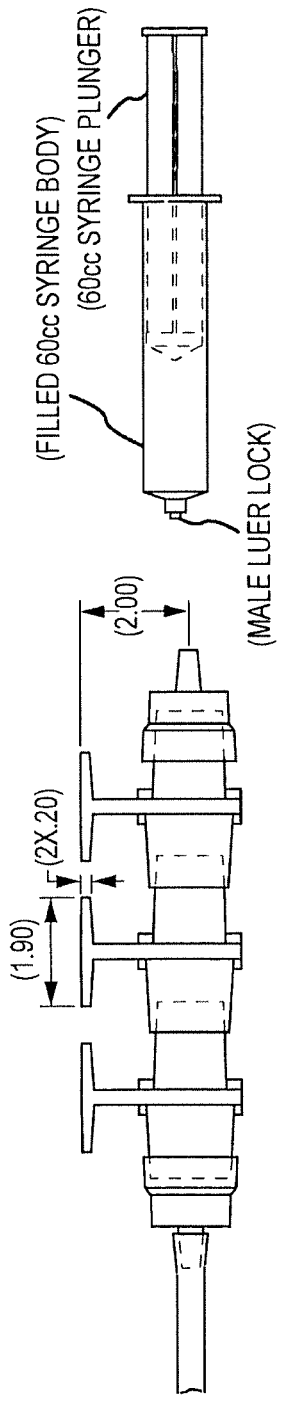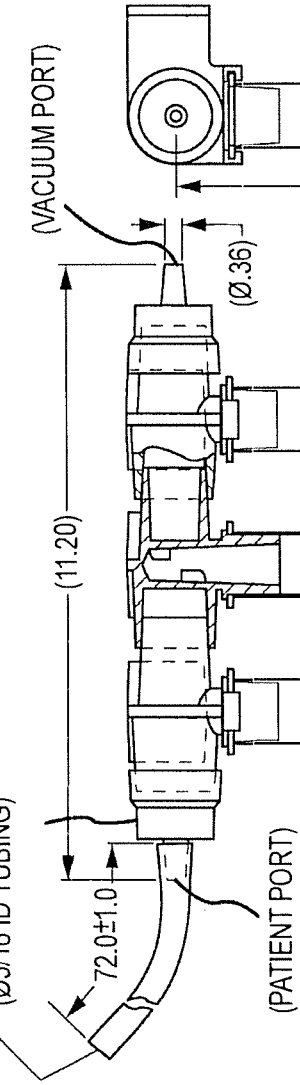

SYRINGE FILL METHOD AND APPARATUS

CROSS REFERENCE TO RELATED APPLICATIONS

This application claims the benefit of U.S. Provisional Application No. 61/725,262, filed Nov. 12, 2012, the entire disclosure of which is hereby incorporated herein by reference in its entirety.

FIELD

A syringe fill method and apparatus are disclosed. More particularly, a modular system and method for filling one or more syringes with tissue, including but not limited to fat, in connection with tissue transfer operations are disclosed.

BACKGROUND

Microlipoinjection is a process in which fat is taken by a cannula from one spot in the body and reinjected in another place in the body. Microlipoinjection has also been known as liposuction with fat transfer, fat grafting or fat transplantation. In general, microlipoinjection is performed to treat divots and scar indentations from trauma to the face or body, such as may occur as a secondary effect of domestic trauma, surgery or infection. Microlipoinjection can also be used to treat the effects of the loss of the subcutaneous layer of fat due to the normal aging process, either alone or in combination with facelift and fat grafting techniques. Other uses for microlipoinjection include providing filler to reapproximate weakened vocal cords, filling sinuses, or partially closing incompetent valves.

In addition, every mass of fat in the human body has with it a varying number of adult stem cells. These stem cells are the precursor to healthy fat cells, and also have a limited ability to differentiate into different tissue. When placed in fat they will divide several times into mature fat cells and more adult stem cells. These stem cells are an important part of a tissue harvest.

Up to about 1990, there were few artificial filler substances available to surgeons. Accordingly, surgeons used human bone, collagen and fat as fillers. However, the use of fat was not very successful, because the instruments and techniques were not sufficiently refined. For example, 50% of the fat may not have lived through the transplantation process. As a result, surgeons would need to implant more fat than would be required if all of the fat survived the process, or the transplantation process would have to be repeated multiple times or both.

More recently, a number of filler substances, such as Restylane Hyaluronic Acid, Collagen, Fibril, ePTFE (Teflon®), Hylan B Gel, Artecol, BioBlastique and have been used. These substances have proved effective at filling small areas, but the cost for larger areas has become prohibitive. For this reason, as well as interest in the "natural substance" concept, surgeons and their patients have again looked at using fat as a filler.

With the renewed interest in using fat as a filler, techniques have been refined to provide a better fat graft "take" with revascularization. However, the instruments and devices conventionally available to perform the procedure remain clumsy and ill-suited for the procedure. For example, conventional systems for transferring fat or other tissue removed from one location in a patient's body to a syringe for reinjection in another location in the patient's body can require multiple steps, expose the tissue to the ambient air, create waste and mess, and are inconvenient.

SUMMARY

Embodiments of the disclosed invention are directed to solving these and other problems and disadvantages of the prior art. In accordance with embodiments of the disclosed invention, a modular collection apparatus is provided. The apparatus features a manifold structure. The manifold structure includes one or more manifold elements. Each manifold element has a coupler for interconnecting a syringe body to the manifold element, optionally includes a barrel or bore for receiving a syringe plunger aligned with the syringe body, an inlet, and an outlet. A barrel inlet and a barrel outlet can also be incorporated, with the barrel inlet offset from the barrel outlet to promote the deposition of tissue into the barrel or body of an attached syringe. A first manifold cap that includes a connector for interconnecting the apparatus to a source of tissue can be joined to the inlet of a first manifold element. A second manifold cap that includes a connector for interconnecting the apparatus to a vacuum source can be joined to the outlet of the last manifold element. In accordance with further embodiments of the present invention, a method for depositing collected tissue into one or more syringes are provided. More particularly, one or more manifold elements and a syringe barrel associated with each of the manifold elements are joined to a source of tissue by a first manifold cap, and to a vacuum source by a second manifold cap. Tissue is drawn through the inlet by a vacuum from the vacuum source. The tissue may be obtained from a patient using a cannula attached to the first manifold cap by a length of flexible tubing. At least some tissue drawn in through the first manifold cap is deposited in a first syringe barrel attached to a first manifold element. The deposition of tissue in the first syringe barrel can be encouraged through the provision of a barrier or wall that prevents the collected tissue from being drawn across the top of the syringe barrel unimpeded. Once the first syringe barrel is full of tissue, any additional tissue drawn in to the apparatus is drawn to a second manifold element and associated syringe barrel (if provided). Accordingly, multiple syringe barrels can be filled sequentially. Once a desired amount of tissue has been collected, the vacuum source can be turned off or disconnected, and the syringe barrel associated with a first manifold element can then be disconnected from the first manifold element. The tissue in the syringe can then be injected into the patient through a needle or cannula attached to the syringe barrel, at the urging of a plunger inserted into the barrel, or deposited into another receptacle for processing.

Additional features and advantages of embodiments of the present invention will become more readily apparent from the following discussion, particularly when taken together with the accompanying drawings.

BRIEF DESCRIPTION OF THE DRAWINGS

FIG. 2A is a top plan view of the modular tissue collection apparatus of the embodiment of FIG. 1;

FIG. 2B is a left side elevation view of the modular tissue collection apparatus of the embodiment of FIG. 1;

FIG. 2C is a rear elevation view of the modular tissue collection apparatus of the embodiment of FIG. 1;

FIG. 2D is a left side elevation view of the syringe element of the modular tissue collection apparatus of the embodiment of FIG. 1;

FIG. 8 illustrates a top plan view of an example construction of a particular embodiment of the modular tissue collection apparatus—the drawing is to scale with dimensions in inches;

FIG. 9 illustrates a left side elevation view of an example construction of a particular embodiment of the modular tissue collection apparatus of FIG. 8 the drawing is to scale with dimensions in inches;

FIG. 10 illustrates a rear elevation view of an example construction of a particular embodiment of the modular tissue collection apparatus of FIG. 8 the drawing is to scale with dimensions in inches; and FIG. 11 illustrates a left side elevation view of the syringe element of an example construction of a particular embodiment of the modular tissue collection apparatus of FIG. 8 the drawing is to scale.

DETAILED DESCRIPTION

Figure 1:
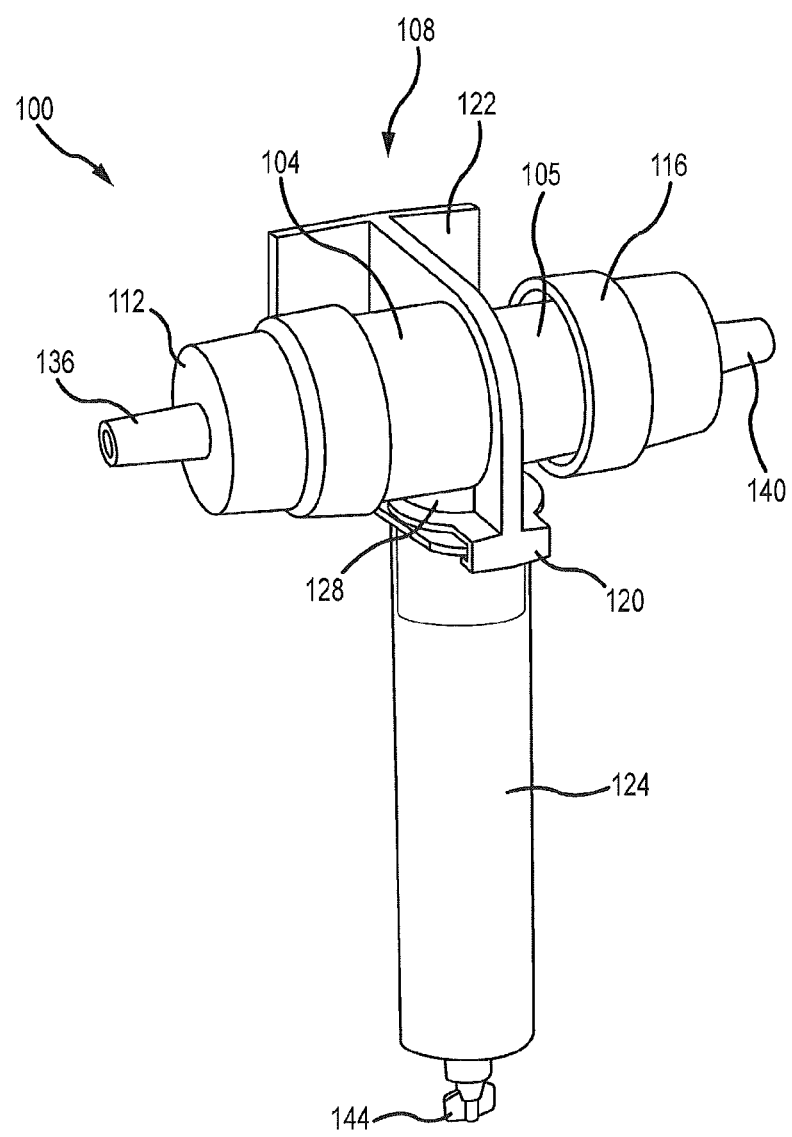
FIG. 1 illustrates a front perspective view of the modular tissue collection apparatus in accordance with an embodiment of the disclosed invention.

A modular tissue collection system or apparatus 100 in accordance with embodiments of the disclosed invention is illustrated in elevation in FIG. 1. The apparatus 100 features a manifold element 108 comprising a coupler 120, manifold barrel or bore 128, manifold input structure 104 and an opposing manifold output structure 105. The manifold input structure 104 connects with a first or inlet manifold cap 112 comprising an inlet orifice 136. The manifold output structure 105 connects with a second or outlet manifold cap 116 comprising an outlet orifice 140. In one embodiment, each of these two afore-mentioned connections are interference fits. Each of the manifold input structure 104 and manifold output structure 105 engage a coupler 120 to which a syringe body or barrel 124 is connected, at least while the apparatus in an assembled state. Each manifold element 108 also includes a plate 122 which may be used, for example, to mount or secure the modular tissue collection apparatus 100 to, for example, a "universal stand" as typical in health care environments. An aperture may optionally be included on the plate 122 itself or proximal to the plate 122, such as on a connecting element between the plate 122 and the manifold element 108, to engage a chain or similar to secure the modular tissue collection apparatus 100.

With a syringe barrel 124 connected to each manifold element 108, the apparatus is sealed from an inlet orifice 136 at the first manifold cap 112 to an outlet orifice 140 at the second manifold cap 116. In a preferred embodiment, when tissue is being collected, the inlet orifice 136 can be connected to a tissue source, for example through a length of flexible tubing and a cannula, and the outlet orifice 140 can be connected to a vacuum source. In another less-preferred embodiment, the tissue flow is reversed, i.e. the outlet orifice 140 can be connected to a tissue source, for example through a length of flexible tubing and a cannula, and the inlet orifice 136 can be connected to a vacuum source. Also, each syringe barrel 124 can be sealed at a tip end by a syringe cap 144, such that the apparatus 100 is completely sealed between the inlet orifice 136 and the outlet orifice 140, at least when the apparatus 100 is configured for tissue collection.

FIGS. 2A-C provide a top plan view, a left side elevation view, and a rear elevation view of the modular tissue collection apparatus of the embodiment of FIG. 1. As shown in FIGS. 2A-C, a modular tissue collection apparatus 100 comprises a manifold input structure 104 engaged with a first manifold cap 112 comprising an inlet orifice 136. The inlet orifice 136 is connected with tubing 150. The tubing 150 may be any commercially available tubing as used, for example, in medical procedures. The tubing 150 fits over an inlet orifice 136 as an interference fit. In other embodiments, the tubing 150 is clamped to the inlet orifice 136 or otherwise engaged so as to maintain a fluid seal. The manifold output structure 105 engages an output manifold cap 116 comprising an outlet orifice 140. The outlet orifice 140 connects to vacuum source (not shown) so as to create suction, or a negative pressure between the inlet orifice 136 and the outlet orifice 140, thereby urging tissue into the modular tissue collection apparatus 100 via the inlet orifice 136. The syringe barrel 124, comprising a syringe cap 144, attaches to the manifold element 108 via a coupler 120. The coupler 120 includes two parallel tracks configured to receive the top of the syringe barrel 124. In other embodiments, the coupler 120 is any means to engage a syringe barrel as known to those skilled in the art, to include a complete or partial ring to enable an interference fit.

Figure 2E:
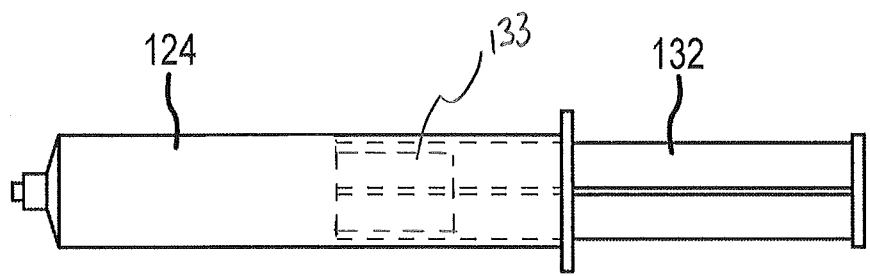
FIG. 2E is a left side elevation view of another embodiment of the syringe element of the modular tissue collection apparatus of the embodiment of FIG. 1.

FIG. 2D is a left side elevation view of the syringe barrel 124 with a syringe plunger 132. In one embodiment, the syringe barrel 124 and/or the syringe plunger 132 are any designs as commercially available. In another embodiment, a distal end of the syringe plunger 132 comprises an outer radial portion, such as a gasket or o-ring, which provides a more secure fit or seal than that typically commercially available. More specifically, an outer radial portion that maintains a fluid seal when receiving a pressure as great as 29.92 inHg (i.e. 1 atm). In another embodiment, the outer radial portion maintains a fluid pressure up to 20 inHg. In another embodiment, the outer radial portion maintains a fluid pressure of approximately 15 inHg FIG. 2E is a left side elevation view of another embodiment of the syringe barrel 124 with a syringe plunger 132. In the embodiment of FIG. 2E, the syringe plunger 132 is specially configured to prevent and/or avoid waste. More particularly, rather than featuring a conventional plunger tip, a hollow tip 133 portion is provided. The volume of the hollow tip 133 allows tissue at the top of the syringe barrel 124 to be trapped, rather than displaced, when the plunger 132 is moved down the manifold element barrel 128, into the syringe barrel 124.

Figure 2F:
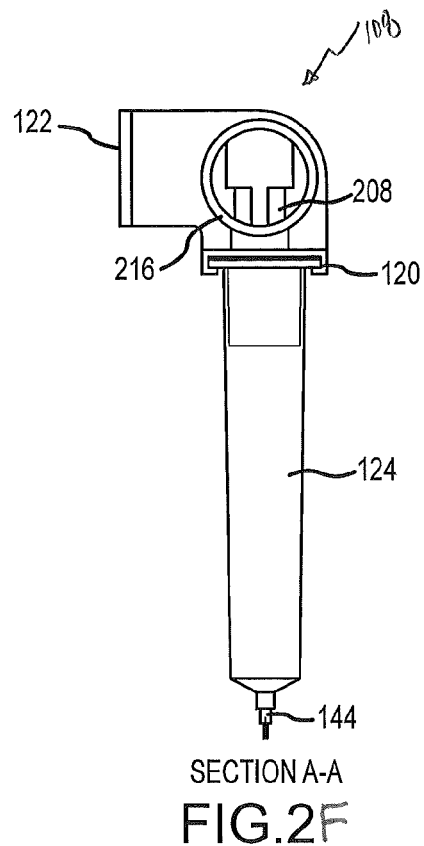
FIG. 2F is a cross-sectional view of section A-A of FIG. 2B.
Figure 2G:
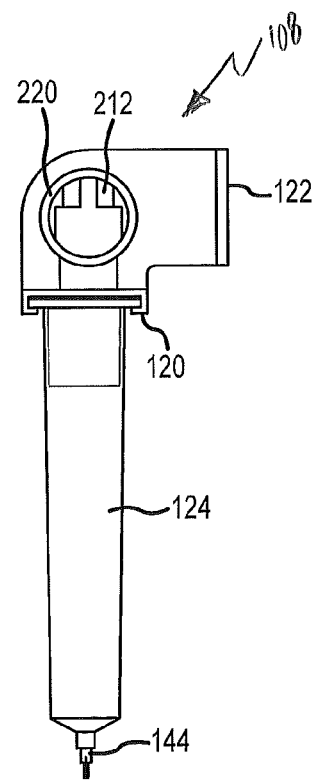
FIG. 2G is a cross-sectional view of section B-B of FIG. 2B.

FIGS. 2F-G illustrate cross-sectional views of sections A-A and B-B, respectively, of FIG. 2B. As shown in FIGS. 2F-G, the modular tissue collection apparatus 100 comprises the manifold element 108 comprising the inlet aperture 216 and the barrel inlet 208, and the outlet aperture 220 and the barrel outlet 212. The barrel inlet 208 at least partially directs or urges incoming or received material, such as tissue, downward into the syringe barrel 124. The vertical offset of the barrel outlet 212 relative to the barrel inlet 208 at least partially directs or urges incoming or received fluid, such as tissue, as received from the inlet orifice 136, to drop into the syringe barrel 124. In some circumstances, for example after the syringe barrel 124 is completely or partially full, the barrel outlet 212 allows received material, such as tissue, to pass toward the outlet aperture.

Figure 3A:
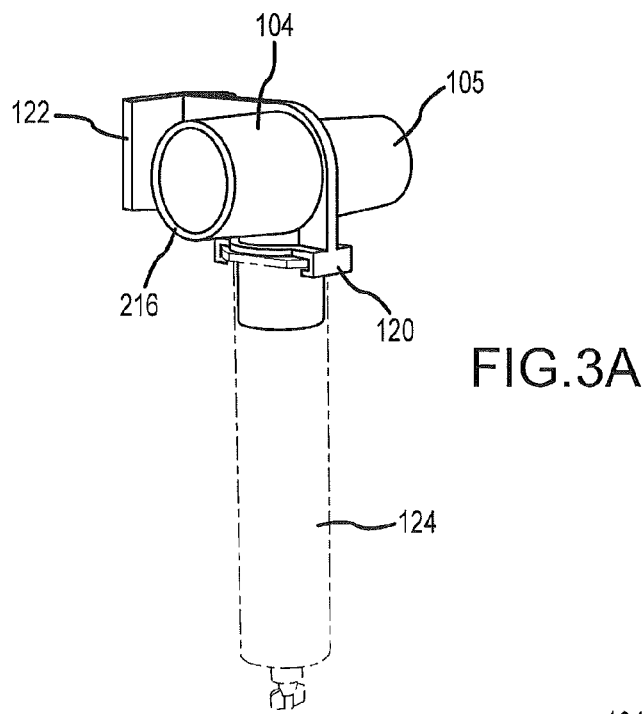
FIG. 3A is a front perspective view of a manifold element of the modular tissue collection apparatus of the embodiment of FIG. 1.
Figure 3B:
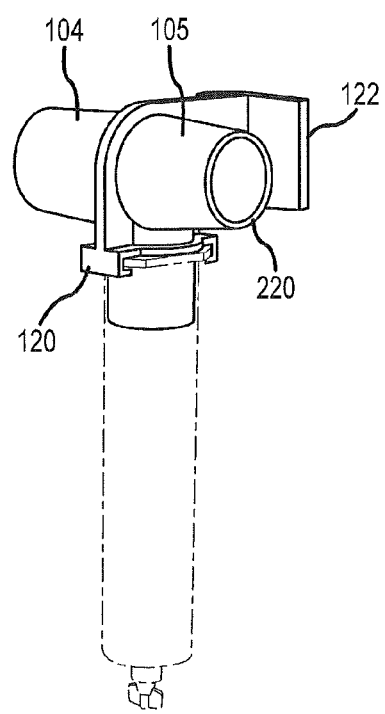
FIG. 3B is a rear perspective view of a manifold element of the modular tissue collection apparatus of the embodiment of FIG. 1.

FIGS. 3A-B illustrate front perspective views of the modular tissue collection apparatus of the embodiment of FIG. 1. The manifold element 108 comprises a manifold input structure 104, a manifold output structure 105 and a coupler 120. The manifold input structure 104 surrounds an inlet aperture 216, with a distal diameter larger than a distal diameter of the outlet aperture 220. Each of the manifold input structure 104 and the manifold output structure 105 taper in external diameter with distance from the coupler 120. In one embodiment, the internal diameters of one or both of the manifold input structure 104 and the manifold output structure 105 similarly taper in diameter with distance from the coupler 120. In another embodiment, each of the manifold input structure 104 and the manifold output structure 105 do not taper and are of constant diameter with distance from the coupler 120.

Figure 4A:
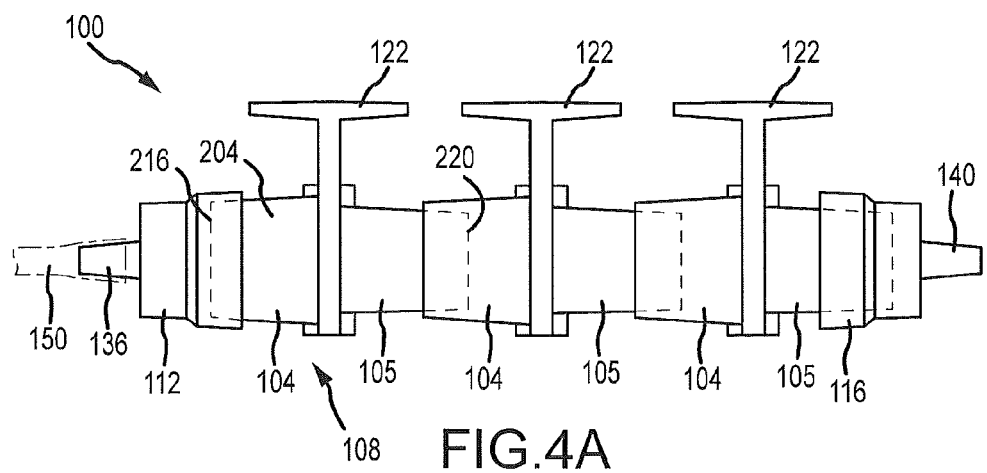
FIG. 4A is a top plan view of the modular tissue collection apparatus in accordance with another embodiment of the present invention.
Figure 4B:
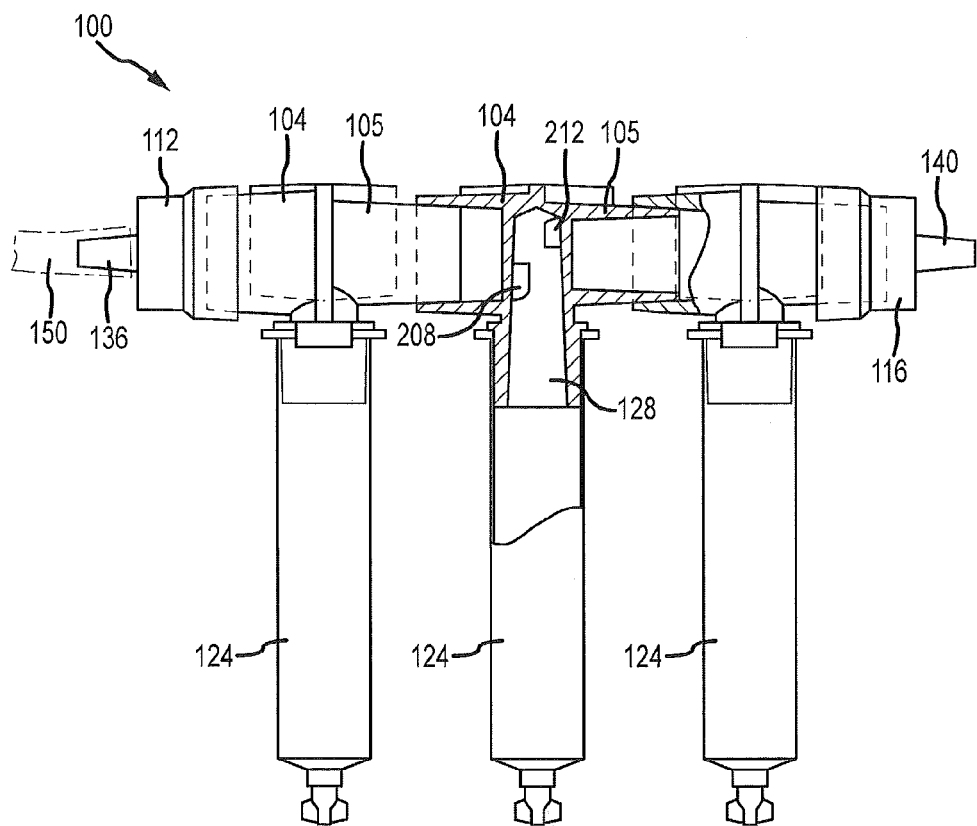
FIG. 4B is a left side partial cross-sectional elevation view of the modular tissue collection apparatus of the embodiment of FIG. 4A.

FIGS. 4A-B illustrate a top plan view, and a left side partial cross-sectional elevation view, respectively, of the modular tissue collection apparatus of the embodiment of FIG. 1 as configured with a plurality of manifold elements 108 and associated syringe barrels 124. The embodiment of FIGS. 4A-B is constructed of the modular components of FIG. 1. A series of three sets of manifold elements 108 with attached syringe barrels 124 is shown. A first manifold cap with an inlet orifice 136 connects with tubing 150 which in turn is engaged with a source of tissue. An outlet manifold cap 116 connects with a vacuum source (not shown) via an outlet orifice 140.

The first manifold element 108 may have an inlet aperture 216 that is joined to the first manifold cap 112, and an outlet aperture 220 that is joined to either the inlet aperture 216 of a second manifold element 108, or to the second manifold cap 116. Accordingly, the manifold structure can be configured with from one to any number of manifold elements 108. Each manifold element 108 includes a coupler 120 to which a syringe body or barrel 124 is connected, at least while the apparatus in an assembled state. With a syringe barrel 124 connected to each manifold element 108, the apparatus is sealed from an inlet orifice 136 at the first manifold cap 112 to an outlet orifice 140 at the second manifold cap 116. When tissue is being collected, the inlet orifice 136 can be connected to a tissue source, for example through a length of flexible tubing and a cannula, and the outlet orifice 140 can be connected to a vacuum source. Moreover, each syringe barrel 124 can be sealed at a tip end by a syringe cap 144, such that the apparatus 100 is completely sealed between the inlet orifice 136 and the outlet orifice 140, at least when the apparatus 100 is configured for tissue collection.

As tissue enters inlet orifice 136 it enters the first of three manifold input structures 112 and the tissue transport channel 204 before reaching the first of three manifold element barrels or bores 128. The entering tissue then engages barrel inlet 208 of the first syringe barrel 124 where it is at least partially directed or urged into the first of three syringe barrels 124. The entering tissue is also urged downward into a particular syringe barrel 124 by gravity. Some tissue may also travel through a manifold element barrel 128 directly toward a downstream manifold output structure 105. Some tissue will travel down into syringe barrel 124, change direction and travel up within manifold element barrel 128 until engaging barrel outlet 212, wherein it will be directed toward manifold output structure 105. The combination of barrel inlet 208 and barrel outlet 212 serve to, among other things, slow the flow of the tissue, akin to a "speed bump" on a roadway.

The manifold structure 104 includes an interior pathway or tissue transport channel 204 that extends from the inlet orifice 136 to the outlet orifice 140. In addition, the tissue transport channel 204 includes features that promote the deposition of tissue into the syringe barrels 124. More particularly, each manifold element 108 includes a barrel inlet 208 that is offset from a barrel outlet 212. In the illustrated example, the barrel inlet 208 of any one manifold element 108 is vertically offset from the barrel outlet 212 of the manifold element 108. In accordance with other embodiments, the barrel inlet 208 can be horizontally offset from the associated barrel outlet 212, or the barrel inlet 208 can be both vertically and horizontally offset from the associated barrel outlet 212.

In accordance with still other embodiments, an additional barrier structure, such as a barrier wall, can be provided to create a circuitous or lengthened path between a barrel inlet 208 and a barrel outlet 212. That is, in one embodiment, the manifold element barrel 128 is configured with a plate or other means or geometry so there is no straight line path between an entry to manifold element barrel 128 and an exit from manifold element barrel 128. Stated another way, the manifold element barrel 128 is configured with a plate, wall or other means or geometry around which material entering the manifold element 108 must flow before exiting manifold element 108, to encourage the depositing of material into the syringe barrel 124.

Figure 5A:
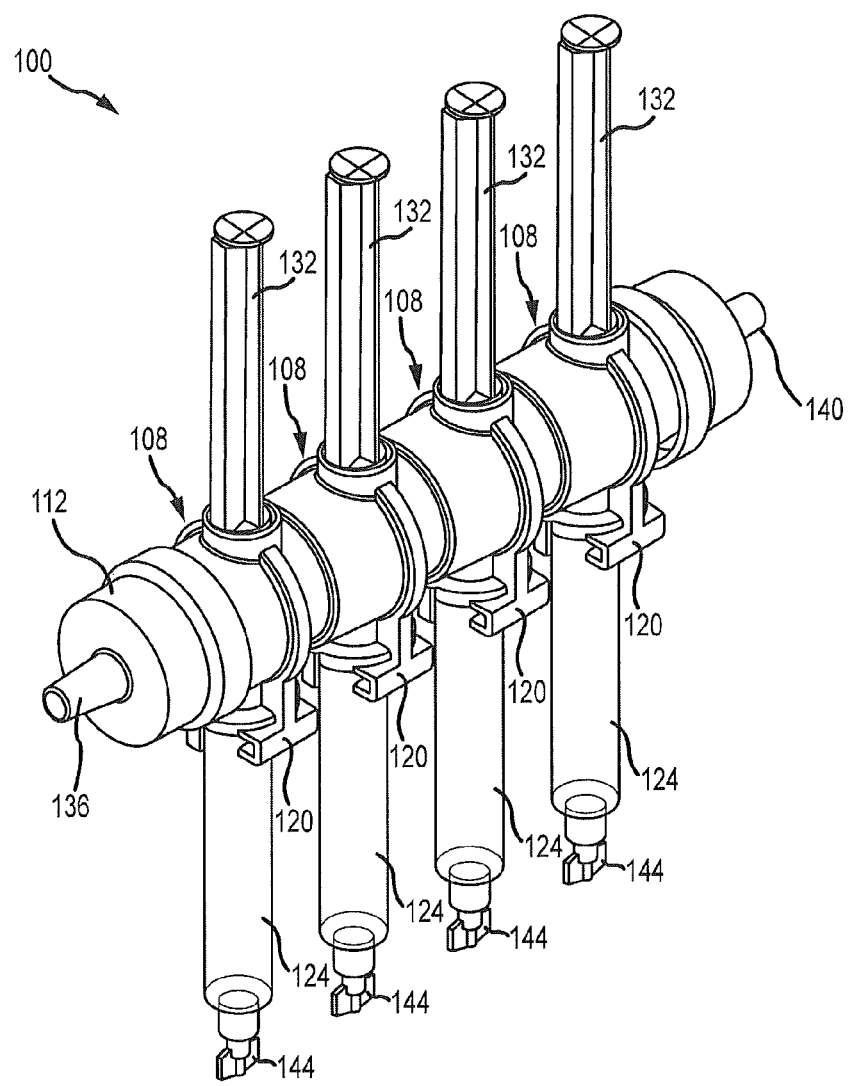
FIG. 5A is a front perspective view of the modular tissue collection apparatus in accordance with another embodiment of the present invention.
Figure 5B:
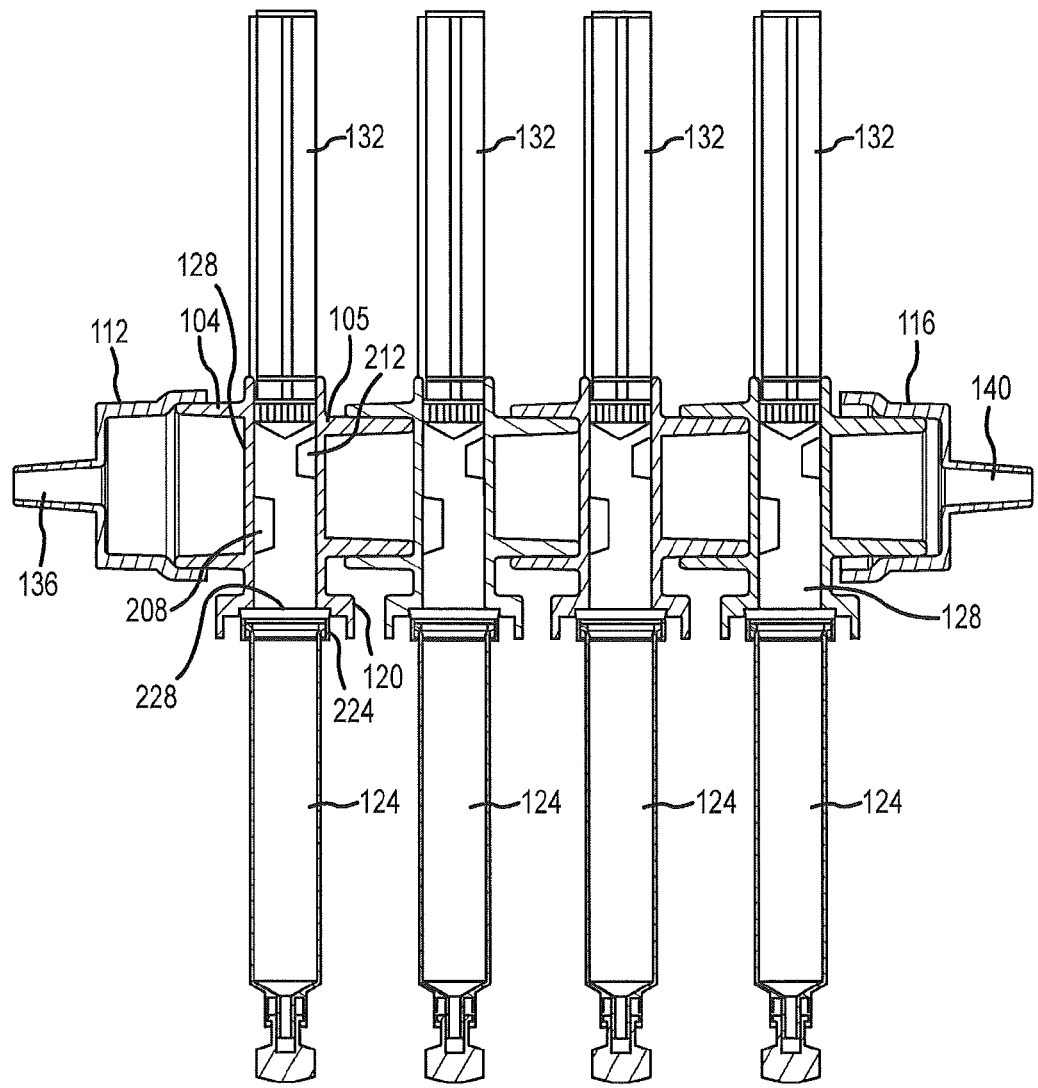
FIG. 5B is a left side cross-sectional elevation view of the modular tissue collection apparatus of the embodiment of FIG. 5A.

FIGS. 5A-B illustrate a front perspective view, and a left side cross-sectional elevation view, respectively, of the modular tissue collection apparatus in accordance with another embodiment of the present invention. The embodiment of FIGS. 5A-B comprises a syringe plunger 132 associated with each syringe barrel 124 and is configured with a plurality of manifold elements 108 and associated syringe barrels 124, syringe caps 144 and syringe plungers 132. A series of four sets of manifold elements 108 are shown. A first manifold cap with inlet orifice 136 connects with tubing (not shown) which in turn is engaged with a source of tissue. An outlet manifold cap 116 connects with a vacuum source (not shown) via outlet orifice 140. As tissue enters inlet orifice 136 it enters the first of four manifold input structures 112 before reaching the first manifold element barrel or bore 128. The tissue then enters barrel inlet 208 where it is at least partially directed or urged into the first of four syringe barrels 124. Some tissue may also travel through manifold element barrel 128 directly toward manifold output structure 105. Some tissue will travel down into syringe barrel 124, change direction and travel up within manifold element barrel 128 until engaging barrel outlet 212, wherein it will be directed toward manifold output structure 105.

The coupler 120 of each manifold element can be configured to receive the finger flanges 224 or other structure of the syringe barrel 124. For example, the finger flanges 224 of syringe barrel can be received in a slotted tab of the coupler 120, forming a bayonet type attachment. An o-ring or other seal 228 can be included at the end of the manifold element barrel 128, to provide an air tight seal between the manifold element 108 and the syringe barrel 124.

Figure 6A:
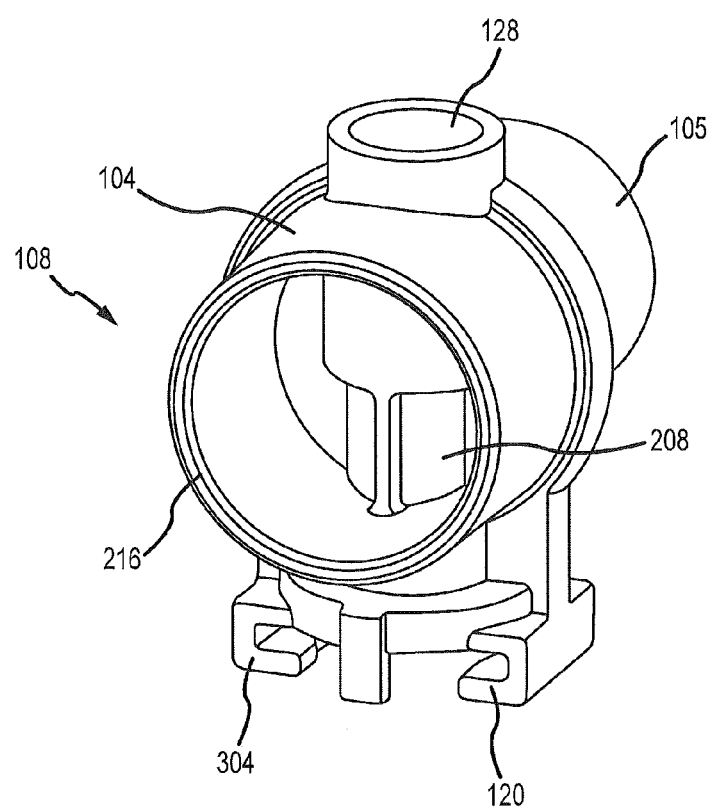
FIG. 6A is a perspective view of a manifold element in accordance with an embodiment of the present invention.

FIG. 6A is a perspective view of a manifold element 108 comprising a manifold input structure 104, a manifold output structure 105, a manifold element barrel 128, a barrel inlet 208 and an inlet aperture 216 in accordance with embodiments of the present invention. In this view, the coupler 120 can be seen to include a pair of slotted tabs 304 for receiving the finger flanges of a syringe barrel 124.

Figure 6B:
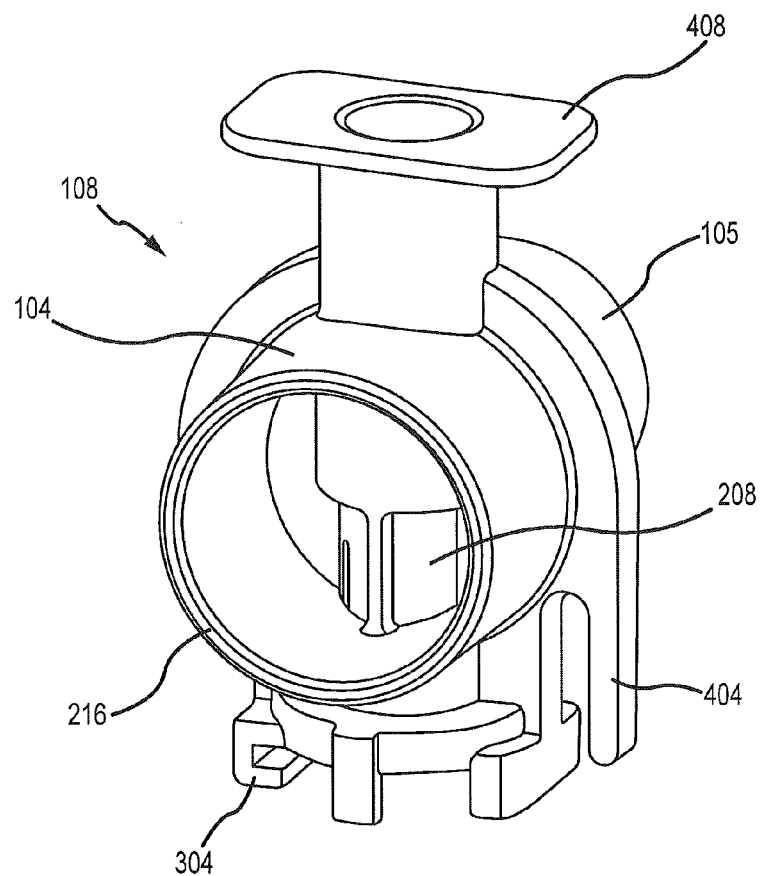
FIG. 6B is a perspective view of a manifold element in accordance with another embodiment of the present invention.

FIG. 6B is a perspective view of a manifold element 108 comprising a manifold input structure 104, a manifold output structure 105, a manifold element barrel 128, a barrel inlet 208 and an inlet aperture 216 in accordance with other embodiments of the present invention. More particularly, the manifold element 108 in this alternative embodiment includes an attachment element 404, for interconnecting the apparatus 100 to a support stand or structure. The example manifold element 108 of FIG. 6B can also feature a finger flange 408, to facilitate the insertion of a syringe plunger 132 into the manifold element barrel 128.

Figure 7:
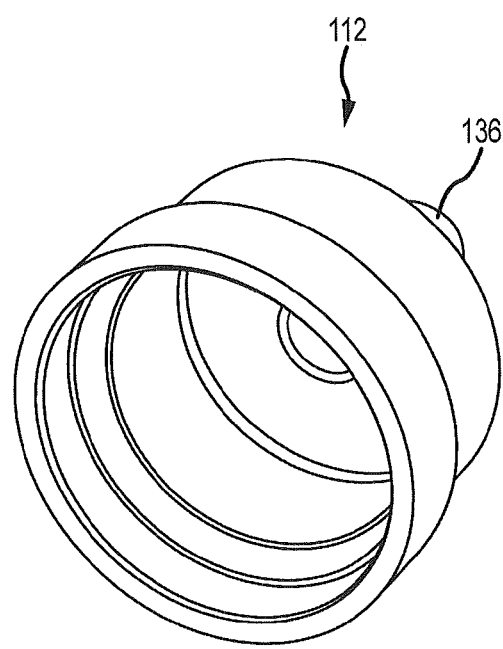
FIG. 7 is a perspective view of a manifold cap in accordance with an embodiment of the present invention.

A first or inlet manifold cap 112 is illustrated in FIG. 7. The inlet orifice 136 may incorporate or be associated with a tip configured to receive a flexible vacuum tube. In accordance with at least some embodiments, the inlet orifice 136 can comprise a Luer lock or other structure for positively interconnecting a vacuum tube to the apparatus 100. In general, the second or outlet manifold cap 116 can appear similar to the inlet manifold cap 112, except that it is dimensioned to attach to the outlet aperture end of a manifold element 108.

As described herein, any number of manifold elements 108 can be included in a tissue collection assembly 100 as described herein. Moreover, each manifold element 108 within a particular manifold structure 104 may be identical to any other manifold element 108 within that structure. Accordingly, a medical practitioner or other user can select the number of manifold elements 108, and thus the number of syringe barrels 124, based on the volume of tissue to be collected and/or transferred during a procedure. In accordance with embodiments of the present disclosure, the syringe barrel 124 sizes can be selected. As can be appreciated by one of skill in the art after consideration of the present disclosure, the sizes of various features of the manifold elements 108 and of the syringe plungers 132 can be varied to match corresponding features of the syringe barrel 124. As examples, but without limitation, syringe barrels 124 with capacities of from 10 cc to 200 cc can be utilized.

In use, the number of manifold elements 108 to be included within the device 100 is selectable. The selected number of manifold elements are then joined together, a first manifold cap 112 is placed over the inlet aperture 204 of the first manifold element 108, and a second manifold cap 116 is placed over the outlet aperture 220 of the last manifold element 108 of the structure 104. In addition, a syringe barrel 124 is connected to the coupler 120, and, in one embodiment, a syringe 132 is placed within the manifold element barrel 128, or each manifold element 108. The inlet orifice 136 of the first manifold cap can then be connected to a tissue source, while the outlet orifice 140 of the second manifold cap can be connected to a vacuum source. A vacuum created by the vacuum source can then be used to draw tissue through the inlet orifice 136, into the manifold assembly 104. As an example, but without limitation, the tissue source can include a deposit of fat within a patient, and tissue comprising fat can be drawn from the patient using a cannula connected to the inlet orifice 136 by a length of vacuum tubing.

As collected tissue is drawn from the inlet orifice 136, towards the outlet orifice 140, the tissue is drawn through the barrel inlet 208 of the first manifold element 108. Gravity then causes at least some of the tissue to drop into the syringe barrel 124 attached to the first manifold element 108. In accordance with embodiments of the present invention, the deposition of tissue in the syringe barrel 124 is promoted by the offset between the the barrel inlet 208 and the barrel outlet 212. Once the first syringe barrel 124 is full of tissue, any additional tissue will be drawn across the top of the syringe barrel 124, out the barrel outlet 212, and to the barrel inlet 208 of the next manifold element 108 (if provided).

Once all or a desired number of syringe barrels 124 have been filled with tissue, either entirely or at least to a desired amount, the application of vacuum by the vacuum source can be discontinued. The syringe barrel 124 can then be disconnected from the coupler 120, for example by rotating the syringe barrel 124 by 90 degrees, and the syringe barrel 124 can be moved so as to draw the syringe barrel 124 down the manifold barrel 128, until it is free from the manifold element 108. The tip 144 can then be removed and, if desired, a needle can be attached to the syringe barrel 124, to enable injection of the collected tissue into the patient. In the embodiment of the modular tissue collection apparatus 100 comprising a syringe plunger 132, after the vacuum source is discontinued, the syringe plunger 132 can be pushed towards an associated syringe barrel 124, down the manifold barrel 128 in which the syringe plunger 132 is received, until the syringe plunger 132 has entered the syringe barrel 124.

In one embodiment of the device, all or portions of the device are manufactured using 3-D printing techniques. In another embodiment, all or portions of the device are made by injection molding techniques.

Although well suited for use in human patients, and although much of the discussion of the present invention is directed toward use involving humans and human tissue, advantages offered by the present invention may be realized in the veterinary and scientific fields for the benefit and study of all types of animals and biological systems.

EXAMPLE

Without intending to limit the scope of the invention, Examples A1-4 depict one example construction of one embodiment of the invention in drawings each to scale. Dimensions are in inches. More specifically, Example A1 illustrates a top plan view, Example A2 a left side elevation view, and Example A3 a rear elevation view of an example construction of a particular embodiment of the modular tissue collection apparatus. Example A4 illustrates a left side elevation view of the syringe element of an example construction of a particular embodiment of the modular tissue collection apparatus of Example A1.

To provide further clarity to the Detailed Description provided herein in the associated drawings, the following list of components and associated numbering are provided as follows:

| # | Component |
|---|---|
| 100 | Apparatus |
| 104 | Manifold Input Structure |
| 105 | Manifold Output Structure |
| 108 | Manifold Element |
| 112 | First Manifold Cap |
| 116 | Outlet Manifold Cap |
| 120 | Coupler |
| 122 | Plate |
| 124 | Syringe Barrel |
| 128 | Manifold Element Barrel or Bore |
| 132 | Syringe Plunger |
| 133 | Hollow Tip |
| 136 | Inlet Orifice |
| 140 | Outlet Orifice |
| 144 | Syringe Cap |
| 150 | Tubing |
| 204 | Tissue Transport Channel |
| 208 | Barrel Inlet |
| 212 | Barrel Outlet |
| 216 | Inlet Aperture |
| 220 | Outlet Aperture |
| 224 | Finger Flanges |
| 228 | Seal |
| 304 | Slotted Tabs |
| 404 | Attachment Element |
| 408 | Finger Flange |

As can be appreciated by one of skill in the art from the present description, embodiments of the present invention provide a convenient means by which tissue collected from a patient can be loaded into one or more syringes, ready for processing and/or reinjection to the patient. Moreover, the collected tissue is protected from contact with the ambient air and/or potential contaminants.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. Features of the invention, such as those disclosed in the embodiments presented, may be combined or eliminated to disclose alternate embodiments of the invention. It is intended that the appended claims be construed to include alternative embodiments to the extent permitted by the prior art.

What is claimed is:

1. A tissue collection system, comprising:
   a first manifold element, including:
      an inlet aperture;
      an outlet aperture;
      a manifold bore;
      a coupler;
   a syringe barrel interconnected to the coupler;
   a first manifold cap, including an inlet orifice, wherein the first manifold cap is connected to the inlet aperture of the first manifold element;
   a second manifold cap, including an outlet orifice, wherein the second manifold cap is connected to the outlet aperture of the first manifold element or an outlet aperture of a second manifold element;
   wherein the inlet orifice is configured to receive tissue,
   wherein a barrel inlet is formed in a side of the manifold bore of the first manifold element adjacent the inlet aperture of the first manifold element,
   wherein a barrel outlet is formed in a side of the manifold bore of the first manifold element adjacent the outlet aperture of the first manifold element, and
   wherein the barrel inlet of the first manifold element is offset from the barrel outlet of the first manifold element.

2. The system of claim 1, wherein the barrel inlet receives tissue from the inlet orifice and urges the tissue into the syringe barrel.

3. The system of claim 2, wherein the tissue entering the barrel inlet is further urged into the syringe barrel by gravity.

4. The system of claim 2, wherein the manifold bore further includes a barrier wall wherein all tissue received by the inlet orifice is directed to the syringe barrel.

5. The system of claim 2, wherein the syringe barrel is in axial alignment with the manifold bore.

6. The system of claim 2, wherein at least one of the first manifold input structure and the first manifold output structure are of tapered cross-section.

7. The system of claim 2, wherein the first manifold element further includes a first manifold input structure comprising the inlet aperture and an inner engagement surface, and a first manifold output structure comprising the outlet aperture and an outer engagement surface.

8. The system of claim 7, wherein the inner engagement surface of a first manifold element is configured to interconnect with an outer engagement structure of a second manifold element and provide a fluid seal therebetween.

9. The system of claim 8, wherein the interconnection between the inner engagement surface of the first manifold element and the outer engagement surface of a second manifold element is an interference fit.

10. The system of claim 7, wherein at least one of the first manifold input structure and the first manifold output structure are of tapered cross-section.

11. The system of claim 10, wherein: i) the first manifold cap is connected to the inlet aperture of the first manifold element by an interference fit, or ii) the second manifold cap in connected to the outlet aperture of the first manifold element or an outlet aperture of a second manifold element by an interference fit.

12. A method for collecting tissue, comprising:
   providing a tissue collection device comprising:
      a first manifold element including an inlet aperture, an outlet aperture, a manifold bore, a barrel inlet formed in a side of the manifold bore adjacent the inlet aperture, a barrel outlet formed in a side of the manifold bore adjacent the outlet aperture, and a coupler, wherein the barrel inlet is offset from the barrel outlet;
      a syringe barrel interconnected to the coupler;
      a first manifold cap including an inlet orifice, wherein the first manifold cap is connected to the inlet aperture of the first manifold element;
      a second manifold cap including an outlet orifice, wherein the second manifold cap is connected to the outlet aperture of the first manifold element or an outlet aperture of a second manifold element;
   fitting the inlet orifice to tubing configured to receive tissue;

positioning a distal end of the tubing proximal to a tissue source wherein the tubing is in communication with the tissue source;

engaging the outlet orifice with a vacuum source wherein the tissue is urged into the inlet orifice toward the vacuum source;

at least partially filling the syringe barrel with tissue;

stopping the urging of the tissue into the inlet orifice by turning off the vacuum source or disengaging the outlet orifice with the vacuum source;

removing the syringe barrel at least partially filled with tissue.

13. The method of claim 12, wherein the inlet aperture is of a first diameter and the outlet aperture is of a second diameter smaller than the first diameter.

14. The method of claim 13, wherein the first manifold element further includes a first manifold input structure comprising the inlet aperture and an inner engagement surface, and a first manifold output structure comprising the outlet aperture and an outer engagement surface, wherein the inner engagement surface of the first manifold element is configured to interconnect with the outer engagement structure of a second manifold element and provide a fluid seal therebetween.

15. The method of claim 14, further comprising:

prior to engaging the outlet orifice with a vacuum source, providing a second manifold element and connecting the outer engagement structure of the second manifold element with the inner engagement surface of the first manifold element, wherein the inlet aperture of the first manifold element and an outlet aperture of the second manifold element are located along a first axis, wherein the barrel inlet of the first manifold element and a barrel inlet of the second manifold inlet are centered on a line that is below the first axis, and wherein the barrel outlet of the first manifold element and a barrel outlet of the second manifold element are centered on a line that is above the first axis; and, prior to stopping the urging of the tissue into the inlet source, at least partially filling the syringe barrel of the second manifold with tissue.

16. A modular tissue collection system, comprising:

a plurality of manifold elements, each including: a manifold input structure with an inner engagement surface and an inlet aperture of a first diameter, a manifold output structure with an outer engagement surface with an outlet aperture of a second diameter smaller than the first diameter, a manifold bore, a coupler, and a syringe barrel interconnected to the coupler, wherein the manifold bore further includes a barrel inlet and a barrel outlet, wherein the barrel inlet is offset from the barrel outlet, wherein the inner engagement surface of a first manifold element is configured to interconnect with the outer engagement surface of a second manifold element and provide a fluid seal therebetween; and an input manifold cap including an inlet orifice, wherein the input manifold cap is connected to the inlet aperture of a first manifold element;

wherein the inner engagement surface of the first manifold element is interconnected with the outer engagement structure of the second manifold element to provide a fluid seal there-between, and wherein the inlet aperture of the first manifold element and the outlet aperture of the second manifold element are centered on a first axis.

17. The system of claim 16, wherein at least one of the manifold input structure and the manifold output structure are of tapered cross-section.

18. The system of claim 17, wherein the interconnection between the inner engagement surface of the first manifold element and the outer engagement surface of the second manifold element is an interference fit.

19. The system of claim 1, wherein the inlet orifice of the first manifold cap and the outlet orifice of the second manifold cap are located along a first axis, wherein the barrel inlet of the first manifold inlet is located on a first side of the first axis, and wherein the barrel outlet is located on a second side of the first axis that is opposite the first side of the first axis.

* * * * *